US011050568B2

(12) United States Patent
Antopolsky et al.

(10) Patent No.: US 11,050,568 B2
(45) Date of Patent: Jun. 29, 2021

(54) SYSTEM FOR ENCRYPTION AND DECRYPTION FILMS OF PERSONAL MEETINGS

(71) Applicants: Eliahu Antopolsky, Zichron Yaakov (IL); Yacov Gottman, Karkur (IL)

(72) Inventors: Eliahu Antopolsky, Zichron Yaakov (IL); Yacov Gottman, Karkur (IL)

(*) Notice: Subject to any disclaimer, the term of this patent is extended or adjusted under 35 U.S.C. 154(b) by 251 days.

(21) Appl. No.: 15/670,026

(22) Filed: Aug. 7, 2017

(65) Prior Publication Data
US 2019/0044722 A1 Feb. 7, 2019

(51) Int. Cl.
H04L 9/32 (2006.01)
G06F 21/60 (2013.01)
G06F 21/62 (2013.01)
H04N 5/76 (2006.01)
H04N 21/6377 (2011.01)
H04N 21/2347 (2011.01)
H04N 21/4408 (2011.01)
H04N 21/4405 (2011.01)
G16H 10/60 (2018.01)
H04L 9/08 (2006.01)
H04N 5/913 (2006.01)
H04N 21/433 (2011.01)

(52) U.S. Cl.
CPC .......... *H04L 9/3231* (2013.01); *G06F 21/602* (2013.01); *G06F 21/6209* (2013.01); *G06F 21/6245* (2013.01); *G16H 10/60* (2018.01); *H04L 9/0866* (2013.01); *H04L 9/0877* (2013.01); *H04N 5/76* (2013.01); *H04N 5/913* (2013.01); *H04N 21/2347* (2013.01); *H04N 21/4405* (2013.01); *H04N 21/4408* (2013.01); *H04N 21/63775* (2013.01); *H04N 21/4334* (2013.01); *H04N 2005/91364* (2013.01)

(58) Field of Classification Search
None
See application file for complete search history.

(56) References Cited

U.S. PATENT DOCUMENTS

| 5,838,792 | A  | * | 11/1998 | Ganesan | H04L 9/0825 380/282 |
| 6,286,098 | B1 | * | 9/2001  | Wenig   | H04L 63/0442 713/151 |
| 6,968,459 | B1 | * | 11/2005 | Morgan  | G06F 12/1408 711/E12.092 |
| 2004/0172307 | A1 | * | 9/2004 | Gruber  | G16H 10/60 705/3 |
| 2005/0114116 | A1 | * | 5/2005 | Fiedler | G11B 27/031 704/201 |
| 2010/0030690 | A1 | * | 2/2010 | Herlitz | G06F 21/6245 705/50 |

(Continued)

*Primary Examiner* — Kaveh Abrishamkar
(74) *Attorney, Agent, or Firm* — B. Aaron Schulman, Esq.; Stites & Harbison, PLLC

(57) ABSTRACT

A recording system that is designed to record a personal meeting between a service provider and a key-holder participant that includes an encryption subsystem, a recording means and a memory means. The recording means films the personal meeting and streams it to the encryption subsystem that encrypts the film and sends it to the memory means. The encryption subsystem includes an encryption means, a decryption means and a key reader. The encrypted film can be decrypted only by using a personal key of the key-holder participant.

12 Claims, 1 Drawing Sheet

(56) References Cited

U.S. PATENT DOCUMENTS

2016/0110504 A1\* 4/2016 Fialkov .................. G06F 19/00
 705/2
2017/0070487 A1\* 3/2017 Greenberg ............ H04W 12/02

\* cited by examiner

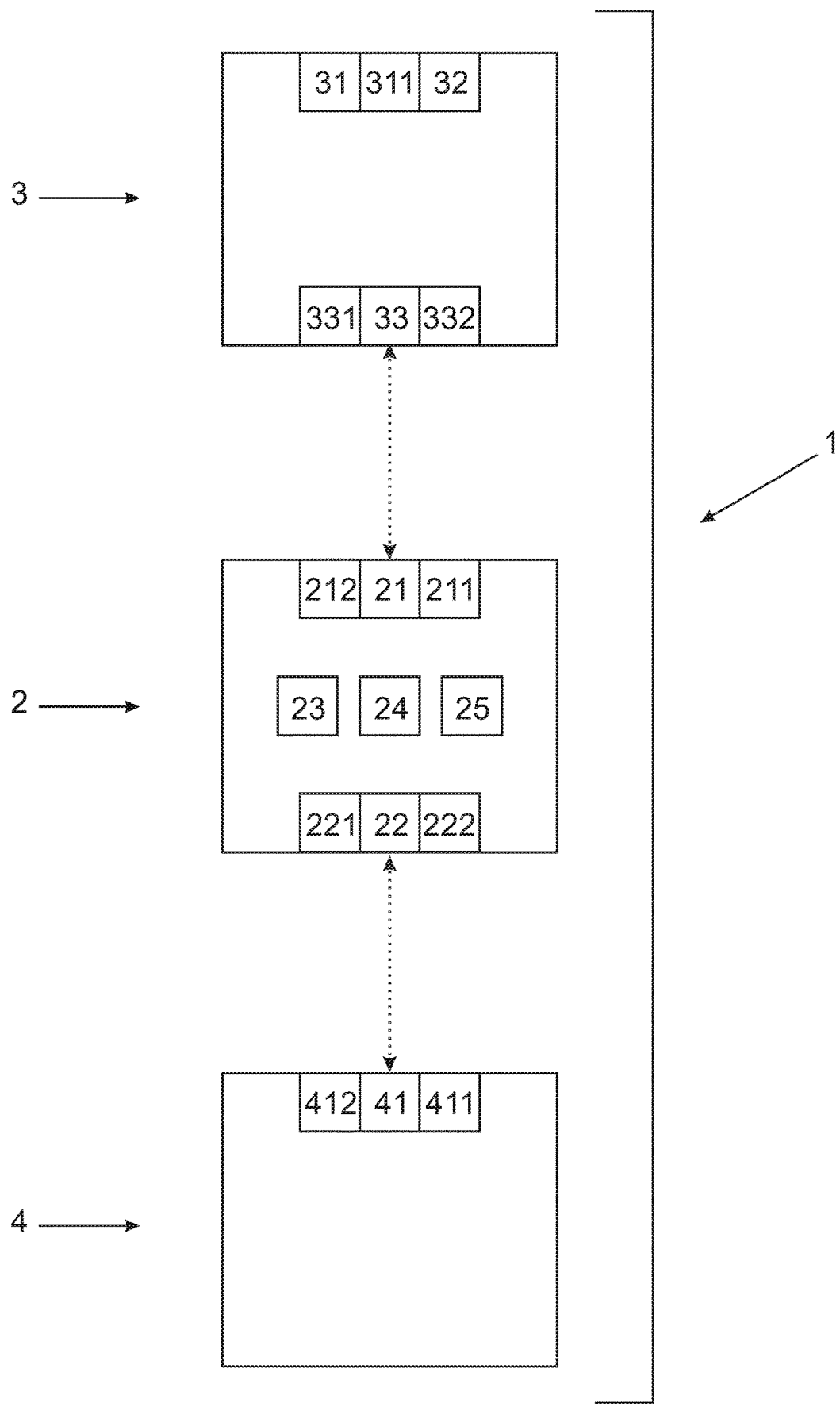

SYSTEM FOR ENCRYPTION AND DECRYPTION FILMS OF PERSONAL MEETINGS

FIELD OF THE INVENTION

The present invention relates to a recording system for encryption and decryption films of personal meetings which enables decryption of said encrypted films only by the consent of key-holder participant using his or her personal key.

BACKGROUND OF THE INVENTION

In many cases disputes arise as to the nature and the content of personal meetings, mainly when such meetings were not recorded and were between two persons in private. Experience of life teaches us that in many such cases one participant alleges ex post facto that during the personal meeting certain events happened or certain spoken words were told and on the other hand the other participant alleges differently. Systems for meeting recordation which include audio and video recordings are known in the art and can provide a satisfying solution in a wide range of cases. However, the solution as described above is not sufficient in special cases, when the key-holder participant has an interest to record the personal meeting and in the same time this recording will be inaccessible to any person without his or her specific consent.

Such kind of personal meetings can be, for example, meetings between psychologist and patient, in which the patient discloses personal and intimate information that he or she does not want this information to be disclosed; meetings of medical treatment, physiotherapy, surgery and other medical treatments in which the patient may expose intimate parts of his or her body; and meetings between attorney and client when they discuss sensitive matters; meetings between people regarding business or any kind of intimate meeting.

The expression "personal meeting" in this patent application and in the claims relates to all of those kind of meetings; The expression "key-holder participant" in this patent application and in the claims relates to the person who has an interest that the recording will not be exposed without his or her permission, for example, the patients and the clients in those personal meetings, who have the interest that the meeting will be recorded while preventing the ability to view the recording without their specific consent; The expression "the service provider" in this patent application and in the claims relates to the persons who participate in the personal meeting other than the key-holder participant, such as the Doctor, the therapist, the lawyer, company manager and the like.

The present invention offers a solution for the service provider and to the key-holder participant who wish to film the personal meetings in a way that will prevent any access to the films unless such access is authorized by a positive action of the key-holder participant. The recording system includes a personal key such that access to the film is possible only when this personal key is used for decryption of the encrypted film. Thus, for instance, the recording system may be used by a therapist and his patients, or by a lawyer and his clients, who wish to document their personal meetings but do not want that the service provider or any other person will be able to access the recording without their specific consent. Also, the service providers may wish to use one recording system for many key-holder participants, for example, dentist who wishes to have such system in his clinic where he provides services to many patients each in his turn. The system, subject matter of the present patent application, offers an excellent solution to this problem. In addition, it is likely that using the system will reduce risks of breach of confidence, negligence, false allegations, and sexual harassment.

LIST OF DRAWINGS

The intention of the drawings attached to the application is not to limit the scope of the invention and its application. The drawings are intended only to illustrate the invention and they constitute only one of its many possible implementations.

FIG. 1 describes schematically the recording system (1) that includes the encryption subsystem (2), the recording means (3) and the memory means (4).

THE INVENTION

The main object of the present invention is to provide a recording system that is designed to film personal meetings between a service provider and a key-holder participant by recording means that includes video and audio means and wherein the film is encrypted by an encryption subsystem and that it is possible to decrypt the encrypted film only by a personal key, which is possessed by the key-holder participant.

The personal meeting can be in fact any kind of meeting. It is possible that the personal meeting will be held between two persons or more. We use the terms "a key-holder participant" and "a service provider" in a singular form but it includes also plural. It is also possible that all the participants will be key-holders and also the service provider. We use the term "service provider" because of that fact that that kind of meeting are highly relevant for this system, but, it is possible that the that person does not provide in fact any service, for example two employees that are used to work together in a specific room and in this case it is possible that only one of them will be the key holder and the second employee will be named the service provider and it is also possible that both of them will be key-holders and this meeting has no service provider.

The recording system (1) subject matter of the present invention includes an encryption subsystem (2), recording means (3) and a memory means (3). The recording means (3) includes a video recording means (32) and may include also a recording voice means (31) that includes a microphone (311). The recording means (3) can be of any kind of a recording voice means and of any kind of video recording means that enables audio and video recording. The recording means (3) also includes a transmitting means (33) for streaming the film to the encryption subsystem (2). The recording system (1) may employ exiting recording means (3) that already exists in the relevant place or in the market. The term transmitting and streaming in this application and in the claims refers to a wireless and wired streaming or transmission. In case of wired streaming the transmitting means (33) includes a port (331), possible USB, for cable that is designed to stream the film to the encryption subsystem (2) and in case of wireless streaming then the transmitting means may include network connector (332). In such case the wireless streaming may be based on Wi-Fi or any other known streaming possibilities preferably on secured protocol.

The memory means (4) in which the encrypted film should be stored can be any kind of standard memory means in local recordation devices, computer workstations, remote servers (cloud storage) and the like. It is possible to use the exiting computers of the relevant place, using remote servers or even to dedicate specific memory means for storing the decrypted film that available in the market. The memory means (4) also includes a receiving means (41) for receiving the encrypted film from the encryption subsystem (2). As mentioned above, the recording system (1) may employ memory means (4) that already exists in the relevant place. The term receiving in this application and in the claims refers to wired and wireless receiving. In case of wired receiving then the receiving means (41) includes a port (411) for cable that is designed to receive the encrypted film from the encryption subsystem (2) and in case of wireless receiving then the receiving means includes a network connector (412). In such case the wireless receiving may be based on Wi-Fi or any other known receiving options.

The encryption subsystem (2) is an essential element of the recording system (1). The encryption subsystem (2) is designed to receive the film of the personal meeting from the recording means (3), to encrypt the film and to stream the encrypted film to the memory means (4). The encryption subsystem (2) also includes a transmitting means (22) for streaming the encrypted film to the memory means (4). In case of wired streaming the transmitting means (22) includes a port (221) for cable that is designed to stream the encrypted film to the memory means (4) and in case of wireless transmission then the transmitting means (22) includes a network connector (222). In such case the wireless streaming may be based on Wi-Fi or any other known transmission options. The encryption subsystem (2) also includes a receiving means (21) for receiving the film from the recording means (3). In case of wired receiving then the receiving means (21) includes a port (211) for cable that is designed to receive the film from the recording means (3) and in case of wireless receiving then the receiving means (21) includes a network connector (212). In such case the wireless receiving may be based on Wi-Fi or any other known receiving options.

The structure of the recording means (3), the memory means (4), and the way and manner that they are connected to the encryption subsystem (2) are understandable from the above explanations to average expert in the field and therefore there is no need for additional details on these matters. In case of wireless streaming it is preferably to use a dedicated secret private network, possible by using built-in routers in the recording system.

The encryption subsystem (2) includes encryption means (23) which is designed to encrypt the film which is received from the recording means (3) and decryption means (24) which is designed to decrypt the decrypted film which is stored in the memory means (4). The encrypted film can be decrypted only by using a personal key of the key-holder participant. Decryption of the encrypted film and access to the information in it can be done only by using the personal key, and consequently only by the active consent and cooperation of the key-holder participant. The key-holder participant possesses the personal key which is designed to decrypt the encrypted film. Thus the key-holder participant of the personal meeting knows that there is no reasonable risk to film the personal meeting due to the fact that the film is encrypted and it is inaccessible to any person without his or her consent and without using the personal key that he or she obtains.

The personal key is a key selected from the group consisting of a password, electronic key, digital key, a key based on magnetic card, a biometric key, a key based on finger print, a key based on retina, or a key based on DNA sample, voice recognition and the like. The encryption subsystem (2) also includes a key reader (25) which is designed to read the personal keys of the key-holder participants. The key reader (25) determines in fact the specific possible type of the corresponding personal key.

The way of using the system (1): For the sake of fluency we will explain this topic by using an example of a Doctor, a treatment room, a patient and a personal key based on finger print. The Doctor (the service provider) installs the system (1) in the treatment room and when starting the personal meeting the patient (the key-holder participant) puts his finger tip (which is his personal key) on the key reader (25) which is in this case a finger print reader. The recording means (3) streams the film to the encryption subsystem (2) that encrypts the film and streams it to the memory means (4). In the end of the personal meeting the patient may use again his fingerprint for ending the process. The encrypted film may be archived in the memory means, in the encryption subsystem or in any other place or media for enabling the service provider or any authorized person to locate these encrypted films and to decrypt them by the encryption subsystem (2) by using the personal key of the patient. If the patient has a complaint as to an event that to his or her allegation has happened during the personal meeting, then as part of the investigation of this complaint, it is possible to summon the patient to locate the encrypted film, to decrypt it with his or her consent and with his or her own presence, using the personal key that he or she possesses, in order to get to the truth.

The service provider can install the recording system (1) in his or her treatment room and to use it for many key-holder participants. The key-holder participants can trust the recording system (1) also due to the fact that it is possible to arrange the encryption subsystem (2) in one visible tangible casing that encrypts the film of his or her personal meeting. It is possible, but not necessarily, that all the components of the encryption subsystem (2) will be in one single casing.

The present invention, as understood from the above explanations, can be related to the encryption subsystem (2) itself, wherein it is designed to communicate with recording means (3) and memory means (4). FIG. 1 describes schematically the recording system (1) that includes the encryption subsystem (2), the recording means (3) and the memory means (4).

What is claimed is:

1. A recording system that records and encrypts a face-to-face personal meeting between at least two key-holder participants who have knowledge in advance of the recording and encrypting of said face-to-face personal meeting and who have consented in advance to have said face-to-face personal meeting recorded and encrypted, each of said at least two key-holder participants having personal keys, and all of said personal keys being required to decrypt said recording, said system comprising:
   an encryption subsystem,
   a recording means that includes a transmitting means, and a memory means;
   wherein said recording means films the face-to-face personal meeting and streams said film by said transmitting means of said recording means to said encryption subsystem;

wherein said encryption subsystem includes a receiving means, an encryption system transmitting means, encryption means, decryption means, and a key reader; and wherein said encryption subsystem receives said film of said face-to-face personal meeting from said transmitting means of said recording means by said receiving means of said encryption subsystem;

wherein said encryption means encrypts said film which is received from the recording means;

wherein said encryption subsystem streams said encrypted film to the memory means by said transmitting means of said encryption subsystem;

wherein said memory means includes a receiving means which is designed for receiving said encrypted film to said memory means; wherein said memory means is designed to store said encrypted film;

wherein said decryption means decrypts the encrypted film; wherein said encrypted film can be decrypted only by using the personal keys of said at least two key-holder participants;

wherein each personal key is a key selected from the group consisting of a password, an electronic key, a digital key, a key based on magnetic card, a biometric key, a key based on finger print, a key based on retina, a key based on DNA sample, and a key based on voice recognition;

wherein said key reader reads the personal keys of at least two key-holder participants;

whereby said recording system can be used for a plurality of key-holder participants;

and whereby access to said encrypted film can be done only by consent of all of said at least two key-holder participants of said personal meeting by using his or her personal key so that said encrypted film is inaccessible to any person without his or her consent and without using his or her personal key; and wherein no one other than the at least two key-holder participants who have knowledge and have consented in advance to have said face-to-face personal meeting recorded and encrypted, each of said at least two key-holder participants having personal keys, and all of said personal keys being required to decrypt said recording, can be enabled to decrypt said recorded face-to-face meeting.

2. The recording system according to claim 1 wherein consent cannot be granted after initiation of the film recording.

3. The recording system according to claim 1 wherein the recording of the meeting must be initiated voluntarily by at least one of the at least two key-holder participants and not by automatic means.

4. The recording system according to claim 1 wherein the film recording is permanently recorded and cannot be overwritten.

5. The recording system according to claim 4 wherein the film recording is not continuous but only takes place from initiation to termination of the face-to-face personal meeting.

6. The recording system according to claim 1 wherein the film recording occurs for the complete duration of the face-to-face personal meeting and is not interrupted during that time.

7. An encryption subsystem that communicates with a recording means which is used to film a personal meeting between at least two participants who have knowledge in advance of the recording and encrypting of said face-to-face personal meeting and who have consented in advance to said film recording and encryption, said encryption system comprising:

a memory means
a receiving means,
a transmitting means,
encryption means,
decryption means and
a key reader;

wherein said encryption subsystem receives film of said personal meeting from said recording means;

wherein said encryption means encrypts said film and to stream said encrypted film to said memory means to be stored;

wherein said memory means receives from said encryption subsystem said encrypted film to be stored;

wherein said decryption means decrypts said encrypted film;

wherein said encrypted film can be decrypted only by using personal keys of all of said at least two participants;

wherein said personal key is a key selected from the group consisting of a password, an electronic key, a digital key, a key based on magnetic card, a biometric key, a key based on finger print, a key based on retina, a key based on DNA sample, and a key based on voice recognition;

wherein said key reader reads said personal keys of all of said at least two participants; and wherein no one other than the at least two participants who have knowledge in advance and who have knowledge of and have consented in advance to said film recording and encryption, can be enabled to decrypt said filmed personal meeting.

8. The encryption subsystem according to claim 7 wherein consent cannot be granted after initiation of the film recording.

9. The encryption subsystem according to claim 7 wherein the recording of the meeting must be initiated voluntarily by at least one of the at least two key-holder participants and not by automatic means.

10. The encryption subsystem according to claim 7 wherein the film recording is permanently recorded and cannot be overwritten.

11. The encryption subsystem according to claim 10 wherein the film recording is not continuous but only takes place from initiation to termination of the face-to-face personal meeting.

12. The encryption subsystem according to claim 7 wherein the film recording occurs for the complete duration of the face-to-face personal meeting and is not interrupted during that time.

* * * * *